United States Patent
Mullins

(10) Patent No.: US 9,996,983 B2
(45) Date of Patent: *Jun. 12, 2018

(54) MANIPULATION OF VIRTUAL OBJECT IN AUGMENTED REALITY VIA INTENT

(71) Applicant: DAQRI, LLC, Los Angeles, CA (US)

(72) Inventor: Brian Mullins, Altadena, CA (US)

(73) Assignee: DAQRI, LLC, Los Angeles, CA (US)

( * ) Notice: Subject to any disclaimer, the term of this patent is extended or adjusted under 35 U.S.C. 154(b) by 6 days.

This patent is subject to a terminal disclaimer.

(21) Appl. No.: 15/171,762

(22) Filed: Jun. 2, 2016

(65) Prior Publication Data

US 2016/0275726 A1 Sep. 22, 2016

Related U.S. Application Data

(63) Continuation of application No. 13/908,621, filed on Jun. 3, 2013, now Pat. No. 9,383,819.

(51) Int. Cl.
*G06F 9/44* (2006.01)
*G06F 9/45* (2006.01)
(Continued)

(52) U.S. Cl.
CPC .............. *G06T 19/20* (2013.01); *G06F 3/011* (2013.01); *G06F 3/013* (2013.01); *G06F 3/015* (2013.01);
(Continued)

(58) Field of Classification Search
CPC ...... G06F 3/04815; G06F 3/016; G06F 3/011; G06F 3/04845; G06F 3/013;
(Continued)

(56) References Cited

U.S. PATENT DOCUMENTS

| 5,759,044 A | 6/1998 | Redmond |
| 6,424,843 B1 * | 7/2002 | Reitmaa .............. H04M 1/0208 379/433.04 |

(Continued)

FOREIGN PATENT DOCUMENTS

| JP | 5985116 B1 | 9/2016 |
| KR | 1020110054376 A | 5/2011 |

(Continued)

OTHER PUBLICATIONS

Ronald Azuma et al., Evaluating Label Placement for Augmented Reality View Management, 2003 IEEE, [Retrieved on Nov. 15, 2017]. Retrieved from the internet: <URL: http://delivery.acm.org/10.1145/950000/946790/20060066.pdf?> 10 Pages (1-10).*

(Continued)

*Primary Examiner* — Anibal Rivera
(74) *Attorney, Agent, or Firm* — Schwegman Lundberg & Woessner, P.A.

(57) ABSTRACT

A system and method for manipulating a virtual object based on intent is described. A reference identifier from a physical object is captured. The reference identifier is communicated via a network to a remote server. The remote server includes virtual object data associated with the reference identifier. The virtual object data is received at the computing device. The virtual image is displayed in a virtual landscape using the virtual object data. In response to relative movement between the computing device and the physical object caused by a user, the virtual image is modified. Brain activity data of the user is received. A state of the virtual object in the virtual landscape is changed based on the brain activity data.

11 Claims, 12 Drawing Sheets

(51) Int. Cl.

| | | |
|---|---|---|
| *G06F 3/01* | (2006.01) | |
| *G06T 19/00* | (2011.01) | |
| *G06T 19/20* | (2011.01) | |
| *G06F 3/0481* | (2013.01) | |
| *G06F 17/30* | (2006.01) | |
| *G06K 9/00* | (2006.01) | |
| *G06F 19/00* | (2018.01) | |
| *G09G 3/00* | (2006.01) | |

(52) U.S. Cl.
CPC ........ *G06F 3/0481* (2013.01); *G06F 17/3087* (2013.01); *G06K 9/00671* (2013.01); *G06T 19/006* (2013.01); *G06F 3/04815* (2013.01); *G06F 19/3418* (2013.01); *G06F 2200/1637* (2013.01); *G06F 2203/011* (2013.01); *G06K 9/00604* (2013.01); *G09G 3/003* (2013.01); *G09G 2340/0492* (2013.01)

(58) Field of Classification Search
CPC . G06F 17/30817; G06F 19/006; G06T 11/00; G06T 11/60; G06B 23/28; H04N 21/44218; H04N 21/42201
See application file for complete search history.

(56) References Cited

U.S. PATENT DOCUMENTS

| | | | |
|---|---|---|---|
| 8,427,508 | B2 | 4/2013 | Mattila et al. |
| 9,030,495 | B2* | 5/2015 | McCulloch .......... G02B 27/017 |
| | | | 345/633 |
| 9,245,388 | B2* | 1/2016 | Poulos .................. G06T 19/006 |
| 9,292,764 | B2* | 3/2016 | Yun ....................... G06K 9/6201 |
| 9,329,677 | B2* | 5/2016 | Chien ..................... G06F 3/011 |
| 9,354,702 | B2 | 5/2016 | Mullins |
| 9,383,819 | B2 | 7/2016 | Mullins |
| 9,449,446 | B1* | 9/2016 | Mullin ................ G07C 9/00158 |
| 2002/0132216 | A1 | 9/2002 | Dohrmann |
| 2006/0058619 | A1* | 3/2006 | DeYoe .................... G06T 11/00 |
| | | | 600/407 |
| 2006/0252979 | A1 | 11/2006 | Vesely et al. |
| 2007/0179646 | A1 | 8/2007 | Dempski et al. |
| 2008/0050711 | A1* | 2/2008 | Doswell ................... G09B 7/02 |
| | | | 434/350 |
| 2008/0071559 | A1 | 3/2008 | Arrasvuori |
| 2008/0191864 | A1* | 8/2008 | Wolfson .................. G06F 3/011 |
| | | | 340/524 |
| 2008/0218472 | A1 | 9/2008 | Breen et al. |
| 2008/0266257 | A1 | 10/2008 | Chiang |
| 2008/0275358 | A1 | 11/2008 | Freer et al. |
| 2009/0096994 | A1* | 4/2009 | Smits .................... G02B 26/101 |
| | | | 353/30 |
| 2009/0113298 | A1 | 4/2009 | Jung et al. |
| 2009/0114079 | A1* | 5/2009 | Egan ..................... G09B 15/023 |
| | | | 84/477 R |
| 2009/0156955 | A1 | 6/2009 | Jung et al. |
| 2009/0327871 | A1 | 12/2009 | Wolf et al. |
| 2010/0207877 | A1 | 8/2010 | Woodard |
| 2011/0018868 | A1 | 1/2011 | Inoue et al. |
| 2011/0018903 | A1 | 1/2011 | Lapstun et al. |
| 2011/0040155 | A1 | 2/2011 | Guzak et al. |
| 2011/0161163 | A1* | 6/2011 | Carlson ................... G06Q 30/02 |
| | | | 705/14.44 |
| 2011/0173576 | A1 | 7/2011 | Murphy et al. |
| 2011/0193858 | A1 | 8/2011 | Lee et al. |
| 2012/0038669 | A1 | 2/2012 | Lee et al. |
| 2012/0089552 | A1* | 4/2012 | Chang ................. G06F 17/30817 |
| | | | 706/52 |
| 2012/0101966 | A1 | 4/2012 | Van Coppenolle et al. |
| 2012/0113209 | A1* | 5/2012 | Ritchey ................... H04N 5/2254 |
| | | | 348/14.02 |
| 2012/0113223 | A1 | 5/2012 | Hilliges et al. |
| 2012/0113228 | A1 | 5/2012 | Konno et al. |
| 2012/0131435 | A1 | 5/2012 | Douris et al. |
| 2012/0188342 | A1* | 7/2012 | Gervautz ................... G06T 7/73 |
| | | | 348/46 |
| 2012/0256954 | A1 | 10/2012 | Soon-shiong |
| 2012/0256956 | A1 | 10/2012 | Kasahara |
| 2012/0289869 | A1 | 11/2012 | Tyler |
| 2012/0290950 | A1 | 11/2012 | Rapaport et al. |
| 2012/0295859 | A1 | 11/2012 | Alexander et al. |
| 2012/0302289 | A1 | 11/2012 | Kang |
| 2013/0009993 | A1 | 1/2013 | Horseman |
| 2013/0013331 | A1 | 1/2013 | Horseman |
| 2013/0042296 | A1 | 2/2013 | Hastings et al. |
| 2013/0063550 | A1* | 3/2013 | Ritchey ................... G03B 37/00 |
| | | | 348/36 |
| 2013/0073978 | A1 | 3/2013 | Butler et al. |
| 2013/0138248 | A1* | 5/2013 | Mathan ............... A61B 5/04842 |
| | | | 700/258 |
| 2013/0169680 | A1* | 7/2013 | Chien ..................... G06F 3/011 |
| | | | 345/633 |
| 2013/0178257 | A1 | 7/2013 | Langseth |
| 2013/0182012 | A1* | 7/2013 | Kim ....................... G06T 19/006 |
| | | | 345/633 |
| 2013/0201215 | A1 | 8/2013 | Martellaro et al. |
| 2013/0241805 | A1* | 9/2013 | Gomez ................... G09G 3/003 |
| | | | 345/8 |
| 2013/0242262 | A1 | 9/2013 | Lewis |
| 2013/0278631 | A1 | 10/2013 | Border et al. |
| 2013/0288761 | A1* | 10/2013 | Santos Paiva Ferraz Conceicao ............. A63F 13/00 |
| | | | 463/7 |
| 2013/0346168 | A1 | 12/2013 | Zhou et al. |
| 2014/0002443 | A1 | 1/2014 | Cunningham |
| 2014/0051510 | A1* | 2/2014 | Benko .................... A63F 13/00 |
| | | | 463/31 |
| 2014/0098134 | A1* | 4/2014 | Fein ....................... G06T 11/60 |
| | | | 345/633 |
| 2014/0139551 | A1* | 5/2014 | McCulloch ........... G02B 27/017 |
| | | | 345/633 |
| 2014/0223462 | A1* | 8/2014 | Aimone ........... H04N 21/42201 |
| | | | 725/10 |
| 2014/0237366 | A1* | 8/2014 | Poulos .................... G06F 3/011 |
| | | | 715/728 |
| 2014/0237495 | A1* | 8/2014 | Jang ................. H04N 21/44218 |
| | | | 725/12 |
| 2014/0240351 | A1* | 8/2014 | Scavezze ................ G06F 3/011 |
| | | | 345/633 |
| 2014/0266646 | A1* | 9/2014 | Urbach .................... G08B 6/00 |
| | | | 340/407.1 |
| 2014/0267005 | A1* | 9/2014 | Urbach .................... G06F 3/016 |
| | | | 345/156 |
| 2014/0267401 | A1* | 9/2014 | Urbach .................... G06T 11/60 |
| | | | 345/633 |
| 2014/0282220 | A1* | 9/2014 | Wantland ............. G06F 3/04845 |
| | | | 715/782 |
| 2014/0313225 | A1* | 10/2014 | Lee ........................ G06T 19/006 |
| | | | 345/633 |
| 2014/0333666 | A1* | 11/2014 | Poulos .................. G06T 19/006 |
| | | | 345/633 |
| 2014/0354532 | A1 | 12/2014 | Mullins |
| 2014/0354534 | A1 | 12/2014 | Mullins |
| 2014/0354685 | A1* | 12/2014 | Lazarow ............. G02B 27/0172 |
| | | | 345/633 |
| 2016/0246371 | A1 | 8/2016 | Mullins |

FOREIGN PATENT DOCUMENTS

| | | |
|---|---|---|
| KR | 1020120133648 A | 12/2012 |
| KR | 1020130014760 A | 2/2013 |
| WO | WO-2014197387 A1 | 12/2014 |
| WO | WO-2014197392 A1 | 12/2014 |

OTHER PUBLICATIONS

E.C. Lalor et al., Steady-State VEP-Based Brain-Computer Interface Control in an Immersive 3D Gaming Environment, 2005 IEEE, [Retrieved on Nov. 15, 2017]. Retrieved from the internet: <URL:

(56) References Cited

OTHER PUBLICATIONS http://delivery.acm.org/10.1145/1290000/1287356/p3156-lalor. pdf> 9 Pages (3156-3164).*
"U.S. Appl. No. 13/908,621 Examiner Interview Summary dated May 4, 2015", 3 pgs.
"U.S. Appl. No. 13/908,621, Advisory Action dated Oct. 6, 2015", 4 pgs.
"U.S. Appl. No. 13/908,621, Final Office Action dated Jun. 18, 2015", 16 pgs.
"U.S. Appl. No. 13/908,621, Non Final Office Action dated Jan. 2, 2015", 16 pgs.
"U.S. Appl. No. 13/908,621, Notice of Allowance dated Mar. 2, 2016", 20 pgs.
"U.S. Appl. No. 13/908,621, Response filed Sep. 17, 2015 to Final Office Action dated Jun. 18, 2015", 12 pgs.
"U.S. Appl. No. 13/908,621, Response filed Oct. 16, 2015 to Advisory Action dated Oct. 6, 2015", 13 pgs.
"U.S. Appl. No. 13/908,621, Response filed Apr. 30, 2015 to Non Final Office Action dated Jan. 2, 2015", 16 pgs.
"U.S. Appl. No. 13/909,042, Examiner Interview Summary dated May 5, 2015", 3 pgs.
"U.S. Appl. No. 13/909,042, Final Office Action dated Jun. 19, 2015", 16 pgs.
"U.S. Appl. No. 13/909,042, Non Final Office Action dated Feb. 4, 2015", 18 pgs.
"U.S. Appl. No. 13/909,042, Notice of Allowance dated Feb. 1, 2016", 23 pgs.
"U.S. Appl. No. 13/909,042, Response filed Oct. 14, 2015 to Final Office Action dated Jun. 19, 2015", 13 pgs.
"U.S. Appl. No. 13/909,042, Response filed May 4, 2015 to Non Final Office Action dated Feb. 4, 2015", 15 pgs.
"Application Serial No. PCT/US2014/040552, International Preliminary Report on Patentability dated Dec. 17, 2015", 6 pgs.
"International Application Serial No. PCT/US2014/040538, International Preliminary Report on Patentability dated Sep. 17, 2005", 4 pgs.
"International Application Serial No. PCT/US2014/040538, International Search Report dated Oct. 20, 2014", 3 pgs.
"International Application Serial No. PCT/US2014/040538, Written Opinion dated Oct. 20, 2014", 6 pgs.
"International Application Serial No. PCT/US2014/040552, International Search Report dated Oct. 21, 2014", 3 pgs.
"International Application Serial No. PCT/US2014/040552, Written Opinion dated Oct. 21, 2014", 4 pgs.
Constantine, Glaros, et al., "Wearable Devices in Healthcare", [Online]retrievedfromtheinternet<URL:http://download.springer. com/static/pdf/543/chp%253 A10, (2005), 28 pgs.
Kevin, M Baird, "Evaluating the Effectiveness of Augmented Reality and Wearable Computing for a Manufacturing Assembly Task", [Online] retrieved from the internet<URL:http://download. springer.com/static/pdf/543/chp%253A10. 1007%252F11311966_8.pdf>, (Jun. 21, 1999), 71 pgs.
"Korean Application Serial No. 10-2015-7037170, Office Action dated 08-30-16", 5 pgs.
"Korean Application Serial No. 10-2015-7037170, Response filed Oct. 31, 2016 to Office Action dated Aug. 30, 2016", W/ English Translation of Claims, 14 pgs.
"New Zealand Application Serial No. 715233, First Examiner Report dated Aug. 18, 2016", 5 pgs.
"European Application Serial No. 14807097.2, Extended European Search Report dated Jan. 11, 2017", 8 pgs.
"U.S. Appl. No. 15/144,545, Non Final Office Action dated Jul. 20, 2017", 18 pgs.
"European Application Serial No. 14807097.2, Response filed Jul. 26, 2017 to Extended European Search Report dated Jan. 11, 2017", 22 pgs.
U.S. Appl. No. 13/908,621, filed Jun. 3, 2013, Manipulation of Virtual Object in Augmented Reality via Intent, now U.S. Pat. No. 9,383,819.
U.S. Appl. No. 13/909,042, filed Jun. 3, 2013, Manipulation of Virtual Object in Augmented Reality via Thought, now U.S. Pat. No. 9,354,702.
U.S. Appl. No. 15/144,545, filed May 2, 2016, Manipulation of Virtual Object in Augmented Reality via Thought.

* cited by examiner

MANIPULATION OF VIRTUAL OBJECT IN AUGMENTED REALITY VIA INTENT

CROSS-REFERENCE TO RELATED APPLICATION

This application is a continuation of U.S. patent application Ser. No. 13/908,621, filed Jun. 3, 2013, which is incorporated by reference herein in its entirety.

TECHNICAL FIELD

The subject matter disclosed herein generally relates to the processing of data. Specifically, the present disclosure addresses systems and methods for manipulating virtual objects in augmented reality via intent.

BACKGROUND

User interfaces on mobile devices with touchscreen often require the user to physically tap or swipe the screen of a mobile device to activate features in applications. Some applications on mobile devices typically require the user to interact with the touchscreen with the user's fingers or stylus to provide input to the applications. When viewing content on a mobile device while holding the mobile device with both hands such as when taking a picture, the user is required to remove one hand from the mobile device to activate a command such as by tapping a photo shutter button in an application.

BRIEF DESCRIPTION OF THE DRAWINGS

Some embodiments are illustrated by way of example and not limitation in the figures of the accompanying drawings.

DETAILED DESCRIPTION

Figure 1:
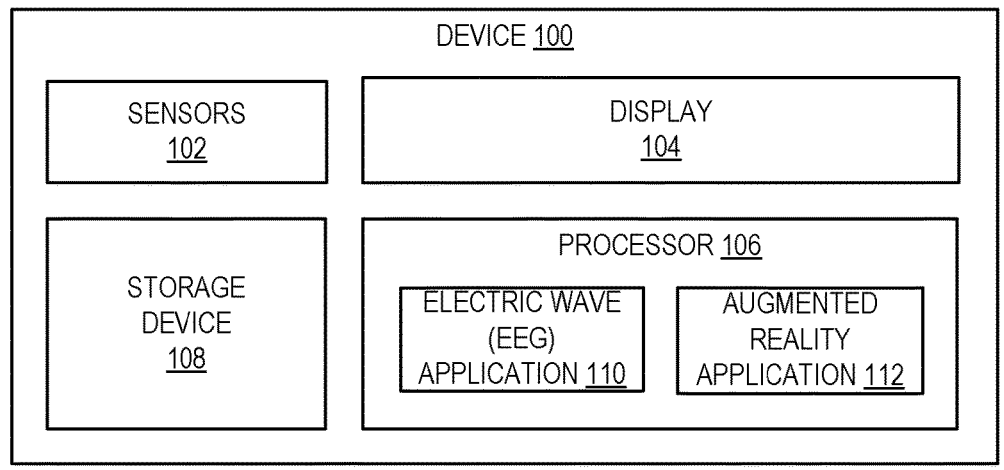
FIG. 1 is a device suitable for enabling selection and manipulation of content based on intent, according to some example embodiments.

Example methods and systems are directed to manipulation of virtual objects in augmented reality based on intent. Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

Augmented reality applications allow a user to experience information, such as in the form of a three-dimensional virtual object overlaid on a picture of a physical object captured by a camera of a device. The physical object may include a visual reference that the augmented reality application can identify. A visualization of the additional information, such as the three-dimensional virtual object overlaid or engaged with an image of the physical object is generated in a display of the device. The three-dimensional virtual object may be selected based on the recognized visual reference. A rendering of the visualization of the three-dimensional virtual object may be based on a position of the display relative to the visual reference.

A system and method for manipulating a virtual object based on intent is described. A reference identifier from a physical object is captured. The reference identifier is communicated via a network to a remote server. The remote server includes virtual object data associated with the reference identifier. The virtual object data is received at the computing device. The virtual image is displayed in a virtual landscape using the virtual object data. In response to relative movement between the computing device and the physical object caused by a user, the virtual image is modified. Brain activity data of the user is received. A state of the virtual object in the virtual landscape is changed based on the brain activity data.

In an example embodiment, a device includes a camera, an augmented reality application, and a brain activity application. The camera captures a reference identifier from a physical object. The augmented reality application communicates the reference identifier via a network to a remote server. The remote server includes virtual object data associated with the reference identifier. The augmented reality application receives the virtual object data at the device, and displays the virtual image in a virtual landscape using the virtual object data. In response to a relative movement between the device and the physical object caused by a user, the augmented reality application modifies the virtual image. The brain activity application receives brain activity data of the user and changes a state of the virtual object in the virtual landscape based on the brain activity data.

In another example embodiment, the device also includes a visual gesture module that determines a focus area in the display and a feature of the virtual object. The visual gesture module then changes a state of the feature in response to the feature being in the focus area of the display. As such, "visual gestures" in a device allow a user to select and activate features in a display of the device without the user having to use his hands to tap on a display of the device. For example, the user makes a "visual gesture" by physically moving and reorienting the device, while the device's camera is displaying real-time images captured from the rear-facing camera of the device. Since the device is overlaying a depicted physical object with a generated virtual object and its features, the physical motions and re-orientations of the device results in a gesture that moves one of the features into the focus area of the display and may result in an action being generated.

In another example embodiment, the visual gesture module determines a focus area in the display and a feature of the virtual object. The visual gesture module then changes a state of the feature in response to the intensity of the output.

In another example embodiment, a storage device includes a database that stores visual references, virtual objects that correspond to the visual references, and features of the virtual objects. Features of the virtual objects are configured to change state in response to the intensity of the output.

In another example embodiment, the focus area corresponds to a predefined portion of the display. The state of the feature changes in response to the feature being located within the predefined portion of the display.

In another example embodiment, the predefined portion of the display comprises at least one of an area central to the display, an area adjacent to an edge of the display, an area adjacent to a corner of the display, or a user-defined portion of a display area.

In another example embodiment, the state of the feature changes in response to the feature being located within the predefined portion of the display for a time duration exceeding a time threshold.

In another example embodiment, the state of the feature changes in response to the intensity of the output exceeding an intensity threshold for a time duration exceeding a time threshold.

In another example embodiment, the visual gesture module comprises a focus area detector and a feature state modifier. The focus area detector detects a presence of the feature of the three-dimensional virtual object in the focus area of the display. The feature state modifier changes a state of the feature in response to the feature being present in the focus area.

In another example embodiment, the feature state modifier changes the state of the feature by replacing a first component of the virtual object in the focus area with a second component of the virtual object in the focus area.

In another example embodiment, a non-transitory machine-readable storage device may store a set of instructions that, when executed by at least one processor, causes the at least one processor to perform the method operations discussed within the present disclosure.

FIG. 1 is a block diagram illustrating a device 100 suitable for enabling selection of content based on visual gestures on the device and intent from a user of the device, according to some example embodiments. The device 100 may include sensors 102, a display 104, a processor 106, and a storage device 108. For example, the device 100 may be a desktop computer, a vehicle computer, a tablet computer, a navigational device, a portable media device, a smart phone of a user, or a user wearable computing device (e.g., glasses). The user may be a human user (e.g., a human being), a machine user (e.g., a computer configured by a software program to interact with the device 100), or any suitable combination thereof (e.g., a human assisted by a machine or a machine supervised by a human).

The sensors 102 may include electrodes that measure electrical activity from a human. For example, the sensors 102 may include electrodes to measure EEG (electroencephalography) waves of brains, EMG (electromyography) waves of muscles, and EOG (electrooculogram) waves of eyes. The sensors 102 can be used to monitor brainwaves through EEG by detecting electrical signals about a person's level of concentration or state of mind. The sensors may be implemented, for example, by using a headset attached to a head of a user. In another example, the sensors 102 can be used to monitor facial muscles to detect facial expressions of the user.

In another example embodiment, the sensors 102 may also include: an optical sensor (e.g., a charged-coupled device (CCD)), an orientation sensor (e.g., gyroscope), and/or an audio sensor (e.g., a microphone). For example, the device 100 may include a front-facing camera for tracking eyes movement and facial expression of the user, and a rear-facing camera for capturing a picture or a video of a physical object (or another displayed virtual object). It is noted that the sensors 102 described herein are for illustration purposes and the sensors 102 are thus not limited to the one described. In another example, sensors 102 may not be physically connected to the device 100 but are instead coupled to the device 100 via wireless means such as Wi-Fi and Bluetooth®.

The display 104 may include, for example, a touchscreen display configured to receive a user input via a contact on the touchscreen display. In another example, the display 104 may include a screen or monitor configured to display images generated by the processor 106. In another embodiment, the display 104 may be transparent or semi-opaque so that the user can see through the display 104.

The processor 106 may include an electric wave (e.g., EEG brain waves) application 110 and an augmented reality application 112. The electric wave application 110 may determine a state of mind (e.g., relaxed, tense, happy, angry) of a user based on outputs from the sensors 102. The state of mind may be based on the intensity or pattern of the outputs of the sensors 102. The augmented reality application 112 may generate a visualization of a virtual object (three-dimensional or two-dimensional) overlaid on an image of a physical object captured by a camera (not shown) of the device 100 in the display 104 of the device 100. The virtual object may be selected based on a present state of mind of the user. The virtual object and features of the virtual object may be further manipulated based on a change in the state of mind of the user. In another embodiment, the virtual object may be further manipulated (e.g., by the user) by adjusting a position of the physical object relative to the camera lens of the device 100. Similarly, the visualization of the virtual object may be manipulated (e.g., by the user) by adjusting a position of the camera lens of the device 100 relative to the physical object.

In one embodiment, the electric wave application 110 may identify the intensity or pattern of electric waves discharged from a human brain over a short period of time. Multiple electrodes may be placed throughout the scalp of a user. Each electrode may be configured to measure different types of waves. For example, Delta waves are most present during sleep. Theta waves are associated with sleep, deep relaxation, and visualization. Alpha waves occur when relaxed and calm. Beta waves occur when actively thinking or problem-solving. Gamma waves occur when involved in higher mental activity and consolidation of information. The electric wave application 110 may then identify a state of mind of the user based on the outputs of the sensors 102. For example, the electric wave application 110 may use EEG electrodes alone or in combination with other sensing devices (microphone, camera, and heart rate monitor).

In one embodiment, the augmented reality application 112 may identify a visual reference on the physical object and tracks the location of the visual reference within the display 104 of the device 100. The visual reference may also be referred to as a marker and may consist of an identifiable image, symbol, letter, number, machine-readable code. For example, the visual reference may include a bar code, a quick response (QR) code, or an image that has been previously associated with the virtual object.

The augmented reality application 112 may generate and display a visualization of the virtual object engaged with an image or picture of the physical object in the display 104. The virtual object may be generated based on the visual reference and the state of mind of the user. Each virtual object may correspond to a unique visual reference and corresponding state of mind (e.g., unique to that virtual object within the augmented reality application 112). In another embodiment, the augmented reality application 112 renders the visualization of the virtual object based a position and an orientation of the device 100 relative to the visual reference in the physical object.

The augmented reality application 112 may determine a focus area in the display 104. The focus area in the display 104 may correspond to a predefined area in the display 104. The predefined area may trigger an action or a change of state in a feature of the virtual object in the display 104. The feature of the virtual object may change state in response to the intensity of the outputs of the sensors 102 or in response to a present state of mind of the user (e.g., user is relaxed). The feature of the virtual object may also change in response to a change of the state of mind of the user (e.g., user is getting more focused). The feature may also change state when the feature is present in in the focus area of the display (e.g., the engine of a displayed virtual car is in the focus area). The focus area may be predefined by the augmented reality application 112 or may be customized and defined by a user of the device 100.

The storage device 108 may be configured to store a database of visual references, virtual objects corresponding to the visual references, features of the virtual objects corresponding to the virtual objects, and corresponding states of mind. The features of the virtual objects can change with the state of mind of the user. For example, the color of the virtual chair can change from blue to red as the user becomes more focused. The virtual chair may be displayed in a blue color if the user is relaxed. In another example, features of the virtual object change when the features are present in the focus area of the display 104. For example, the visual reference may include a machine-readable code or a previously identified image (e.g., a picture of shoe). The previously identified image of the show may correspond to a three-dimensional virtual shoe that can be viewed from different angles by manipulating the position of the device 100 relative to the picture of the shoe. Features of the three-dimensional virtual shoe may include selectable icons on the three-dimensional virtual shoe. An icon may be selected or activated by moving (e.g., repositioning, reorienting, or both) the device 100 to display the icon within a focus area of the display 104. For example, the focus area may be a central area of the display 104, a corner of the display 104, an edge of the display 104, or any suitable combination thereof.

In one embodiment, the device 100 may communicate over a network (not shown) with a server (not shown) to retrieve a portion of the database of visual references, corresponding three-dimensional virtual objects, corresponding features of the three-dimensional virtual objects, and corresponding states of mind. The network may be any network that enables communication between or among machines, databases, and devices (e.g., the device 100). Accordingly, the network may be a wired network, a wireless network (e.g., a mobile or cellular network), or any suitable combination thereof. The network may include one or more portions that constitute a private network, a public network (e.g., the Internet), or any suitable combination thereof.

Any one or more of the modules described herein may be implemented using hardware (e.g., a processor of a machine) or a combination of hardware and software. For example, any module described herein may configure a processor to perform the operations described herein for that module. Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices.

Figure 2:
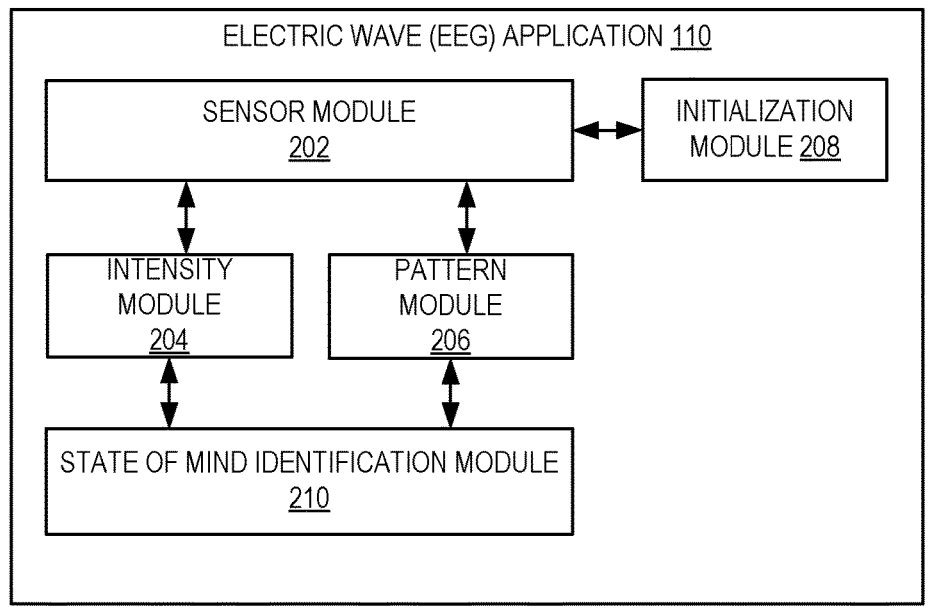
FIG. 2 is a block diagram illustrating modules (e.g., components) of an electric wave application in the device of FIG. 1, according to some example embodiments.

FIG. 2 is a block diagram illustrating modules (e.g., components) of the electric wave application 110 in the device 100, according to some example embodiments. The electric wave application 110 may include a sensor module 202, an initialization module 208, an intensity module 204, a pattern module 206, and a state of mind identification module 210.

The sensor module 202 captures outputs from the sensors 102. For example, the sensor module 202 may capture electric waves generated by a brain of the user by using EEG electrodes positioned on the scalp of the user. As previously described, the sensor module 202 may also capture outputs from other types of sensors such as a heart rate monitor or a facial muscle monitor to further supplement outputs from the EEG electrodes. In another embodiment, the sensors 102 may include a camera to detect the gaze of the user and determine where the user is look on the display 104.

The initialization module 208 enables the electric wave application 110 to initialize and calibrate outputs from sensors 102 based a particular user. The user may be asked to relax while the initialization module 208 captures a sample of outputs from the sensors while the user in a relaxed state of mind. The sample outputs may then be used as a baseline or a reference for the user.

The intensity module 204 measures the intensity of one or more sensors. For example, the intensity module 204 may measure the intensity of electrical signals of Alpha waves in combination with the heart rate of a user to determine the user's relaxed state of mind. In another embodiment, the intensity may be based on a statistical computation (e.g., average or median) of one or more outputs from selected sensors.

The pattern module 206 measures a pattern of a combination of EEG electrodes or sensors. For example, a user may generate a unique brainwave pattern when the user is thinking about a specific car. The pattern module 206 may record the pattern of the outputs of the sensors 102 and associate the unique pattern from the user with the specific car. In another embodiment, the pattern module 206 identifies the pattern based on one or more outputs from selected or most relevant sensors. For example, the pattern module 206 may identify a unique combination of brain wave pattern when the user is looking at a car in the display. The pattern module 206 determines that the user is looking at the car using an optical sensor or a camera of the device 100. Outputs from electric waves associated with muscles of a user may also be used in combination with brain EEG to further increase the identification of unique pattern (e.g., alpha brain wave pattern A, delta bran wave pattern B, facial muscle pattern C, and eyes looking at object D in the display). As such, each unique pattern from the user may be associated with a unique visualization of a virtual object experience. In other words, a unique pattern of sensors 102 trigger an identification of a specific virtual object to be visualized in the display 104.

The state of mind identification module 210 may thus determine and identify a state of mind of the user based on brain activity data from the intensity module 204 and the pattern module 206. For example, the state of mind identification module 210 may determine that the user is happy, relaxed, angry, focused, hungry, or thirsty. In another embodiment, the state of mind identification module 210 may determine a change in the state of mind of the user based on changes from the intensity module 204 and from pattern module 206. For example, the state of mind identification module 210 may determine that the user who was previously relaxed is becoming tense.

Figure 3:
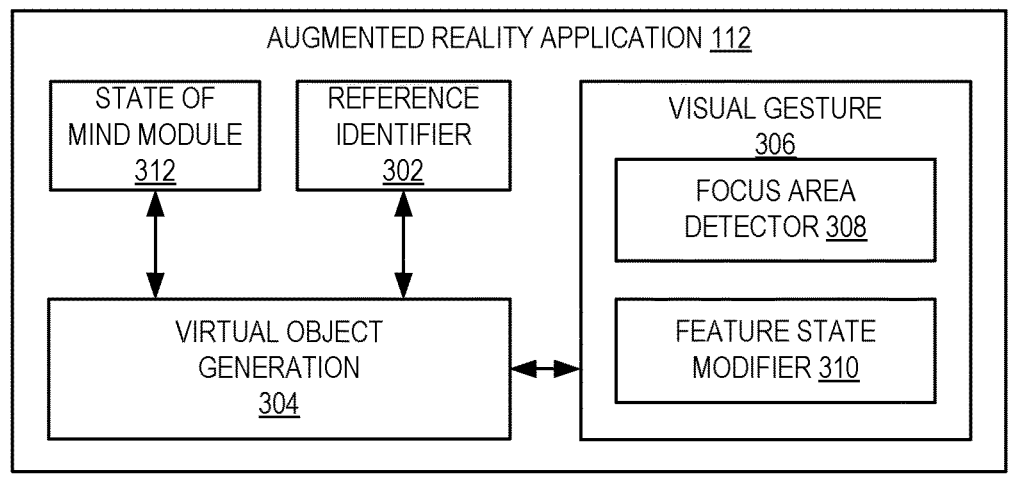
FIG. 3 is a block diagram illustrating modules (e.g., components) of an augmented reality application in the device of FIG. 1, according to some example embodiments.

FIG. 3 is a block diagram illustrating modules (e.g., components) of the augmented reality application 112 in the device 100, according to some example embodiments. The augmented reality application 112 may include a reference identifier module 302, a state of mind module 312, a virtual object generation module 304, and a visual gesture module 306.

The state of mind module 312 generates a state of mind of a user based on the state of mind identification module 210 of the electric wave application 110. For example, the state of mind module 312 may indicate that the user is relaxed. The state of mind module 312 may also identify that a change in the state of mind of the user based on the state of mind identification module 210.

The reference identifier module 302 identifies a visual reference on a physical object captured by sensors 102 of the device 100. For example, a camera of the device 100 captures an image of a physical object, such as a page on a newspaper. The page on the newspaper may include an article and a picture. The picture may have been already identified as a visual reference in the storage device 108. The picture may be associated with a corresponding three-dimensional model of an object (e.g., a virtual sofa).

The virtual object generation module 304 generates and displays a visualization of a three-dimensional virtual object engaged with an image of the physical object captured by the sensor 102 of the device 100 (e.g., the virtual sofa floats and rotates on top of the magazine page). The virtual object may be based on the visual reference (e.g., a furniture ad in the magazine page). In one embodiment, each virtual object may be uniquely associated with a visual reference. The virtual object generation module 304 renders the visualization of the virtual object based a position of the device 100 relative to the visual reference. In another embodiment, attributes of the virtual object may be based on the state of mind of the user. For example, the virtual object generation module 304 may generate a blue color sofa when the state of mind of the user indicates that the user is relaxed. Similarly, the virtual object generation module 304 may generate a red color sofa when the state of mind of the user indicates that the user is excited.

In yet another embodiment, the virtual object generation module 304 generates a virtual object based on a change in the state of mind of the user. For example, a blue color car may morph into a red color sofa when the state of mind of the user indicates that the user is getting more excited.

The visual gesture module 306 may determine a focus area in the display 104 and a feature of the virtual object. For example, those features may include points of interest or user-interactive objects on a three-dimensional virtual object. For example, the three-dimensional virtual object may include a three-dimensional floor plan with icons corresponding to points of interest in the three-dimensional floor plan. An icon located in a room represented in the three-dimensional floor plan may be activated to generate more information (size of the room, description of the room, etc.) about the corresponding room. The icon may be activated by the user tapping on the representation of the icon on the display 104.

In one embodiment, the visual gesture module 306 may change a state of the feature or activate the feature when the feature is in the focus area of the display or based in response on the user state of mind. For example, the focus area may be set as a center area in the display 104. Using the previous example, the user may move the device 100 so that the icon of a room of interest may be displayed in the center area in the display 104. The visual gesture module 306 may change the color or shape of the icon to indicate the user that the icon has been selected. In another example, the room of interest may be highlighted in red based on the user state of mind indicating that the user is excited.

Furthermore, if the user maintains the icon in the center area of the display 104 for at least a predetermined amount of time (e.g., a few seconds), the icon may change state or otherwise be activated to initiate an action corresponding to taping on the icon. For example, a dialog box may be generated in the display to provide a description of the room selected by the user.

In another embodiment, the visual gesture module 306 includes a focus area detector 308 and a feature state modifier 310. The focus area detector 308 detects a presence of the feature of the virtual object in the focus area of the display 104. The focus area detector 308 may track an eye movement of the user looking at the device 100 to determine a specific area in the display where the user is looking at. For example, the focus area detector 308 may determine based on a motion, an orientation, and a position of the device 100 relative to the user and the physical object that the user is looking at a particular area in the display 104. The focus area detector 308 may also use one or more camera lenses in the device facing the user to extrapolate the position and a movement of the eyes of the user and thus the corresponding area on the display 104 at which the user is looking.

The feature state modifier 310 may be configured to change a state of the feature when the feature is present in the focus area of the display 104. For example, the feature state modifier 310 may activate a feature corresponding to an area that the user is looking at using the eye tracking feature previously described. In another example, the focus area detector 308 determines that the user is excited when looking at a particular room in a floor plan displayed in the display 104. The virtual object generation module 304 may generate a virtual three-dimensional model of the particular room with bright wall colors.

Figure 4:
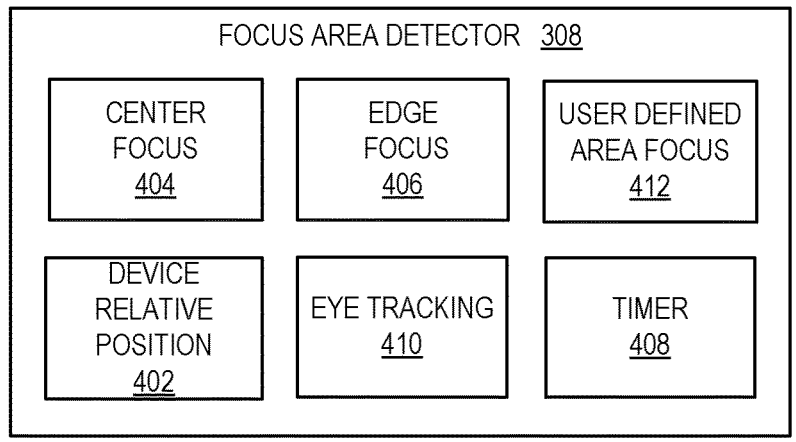
FIG. 4 is a block diagram illustrating modules (e.g., components) of a focus area detector of the augmented reality application of FIG. 3, according to some example embodiments.

FIG. 4 is a block diagram illustrating modules (e.g., components) of a focus area detector 308 of the visual gesture module 306, according to some example embodiments. The focus area detector 308 may include a device relative position module 402, a center focus module 404, an edge focus module 406, a timer module 408, an eye tracking module 410, and a user-defined area focus module 412.

The device relative position module 402 may be configured to detect the position and the orientation of the device 100 relative to the visual reference on the physical object by using the sensor 102. For example, a gyroscope may determine the orientation and position of the device 100. A camera can be used to determine the aim and angle of the device 100 relative to the visual reference. In other words, the device relative position module 402 determines how far or how close the device 100 is to the visual reference and how the device 100 is aimed at the visual reference.

In another embodiment, the device relative position module 402 detects an orientation of the device. For example, the device relative position module 402 may detect whether the device 100 is held in a landscape mode or portrait mode. The location of the focus area may depend on whether the device 100 is held in landscape mode or portrait mode. Further, features of the three-dimensional virtual object may be enabled or disabled based on whether the device 100 is held in landscape mode or portrait mode.

The center focus module 404 may be configured to define the focus area of the display 104 in the center of display 104. For example, the center focus module 304 may be configured to define an area in about the center of the display 104 as the focus area. The area may be in the shape of a circle, oval, or any other shape. The area may be predefined by the visual gesture module 306 or may be customized based on a user selection. For example, the user may be able to move the focus area to another area in the display 104.

The edge focus module 406 may be configured to define the focus area of the display 104 at an edge of the display 104. For example, the edge focus module 406 may be configured to define an area at an edge or in a corner of the display 104 as the focus area. The area may be in the shape of a circle, oval, or any other shape. The area may also be predefined by the visual gesture module 306 or may be customized based on a user selection. For example, the user may be able to move the focus area to another area in the display 104.

The timer module 408 may be configured to measure the amount of time the device 100 has been pointed to the visual reference such that a feature of the virtual object is located within a focus area of the display 104.

The eye tracking module 410 may be configured to track an eye movement of the user looking at the device 100 to determine an area in the display of the device 100 where the user is looking.

The user-defined area focus module 412 may be configured to enable the user to define and select any portion of area or any shape of area in the display 104 to be used a focus area.

Figure 5:
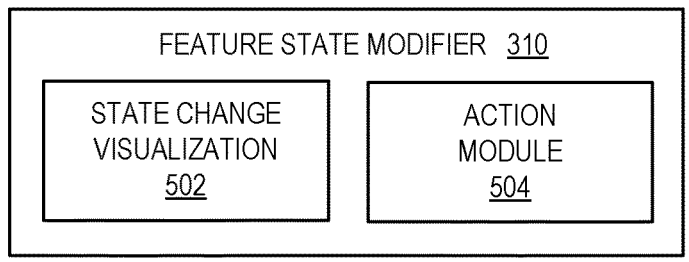
FIG. 5 is a block diagram illustrating modules (e.g., components) of a feature state modifier of the augmented reality application of FIG. 3, according to some example embodiments.

FIG. 5 is a block diagram illustrating modules (e.g., components) of the feature state modifier 310 of the visual gesture module 306, according to some example embodiments. The feature state modifier 310 may be configured to change a state of a feature present in a focus area in the display 104 as previously described. For example, if the focus area is in a center area of the display 104, the feature state modifier module 310 may change the color of the icon to indicate the user that the icon has been selected when the focus area detector 308 detects that the user has maintained the icon in the center area of the display 104 for at least a predetermined amount of time (e.g., a few seconds). In that case, the icon may change state or otherwise be activated to initiate an action corresponding to taping on the icon. For example, a dialog box may be generated in the display to provide a description of the room selected by the user.

In another example, the feature state modifier module 310 may change the color of the icon to indicate the user that the icon has been selected when the focus area detector 308 detects that the user has maintained the icon in the center area of the display 104 for at least a predetermined amount of time (e.g., a few seconds) and when the state of mind module 312 determines that the user has maintained a particular state of mind for at least a predetermined amount of time (e.g., a few seconds).

The feature state modifier 310 may include a state change visualization module 502, and an action module 504. The state change visualization module 502 may be configured to change an icon in the focus area. For example, the color or shape of the icon may change, or the icon may be replaced with another icon or another user interface such as a notification box.

The action module 504 may be configured to trigger an action similar to tapping on the icon on the display 104. For example, the action module 504 may generate a message notification, a dialog box, a menu, or any other action triggered by the presence of the feature in the focus area in the display 104 or by the state of mind of the user. In another embodiment, the action module 404 may be configured to generate a communication from the device 100 to another device, for example, via a wireless network.

Figure 6A:
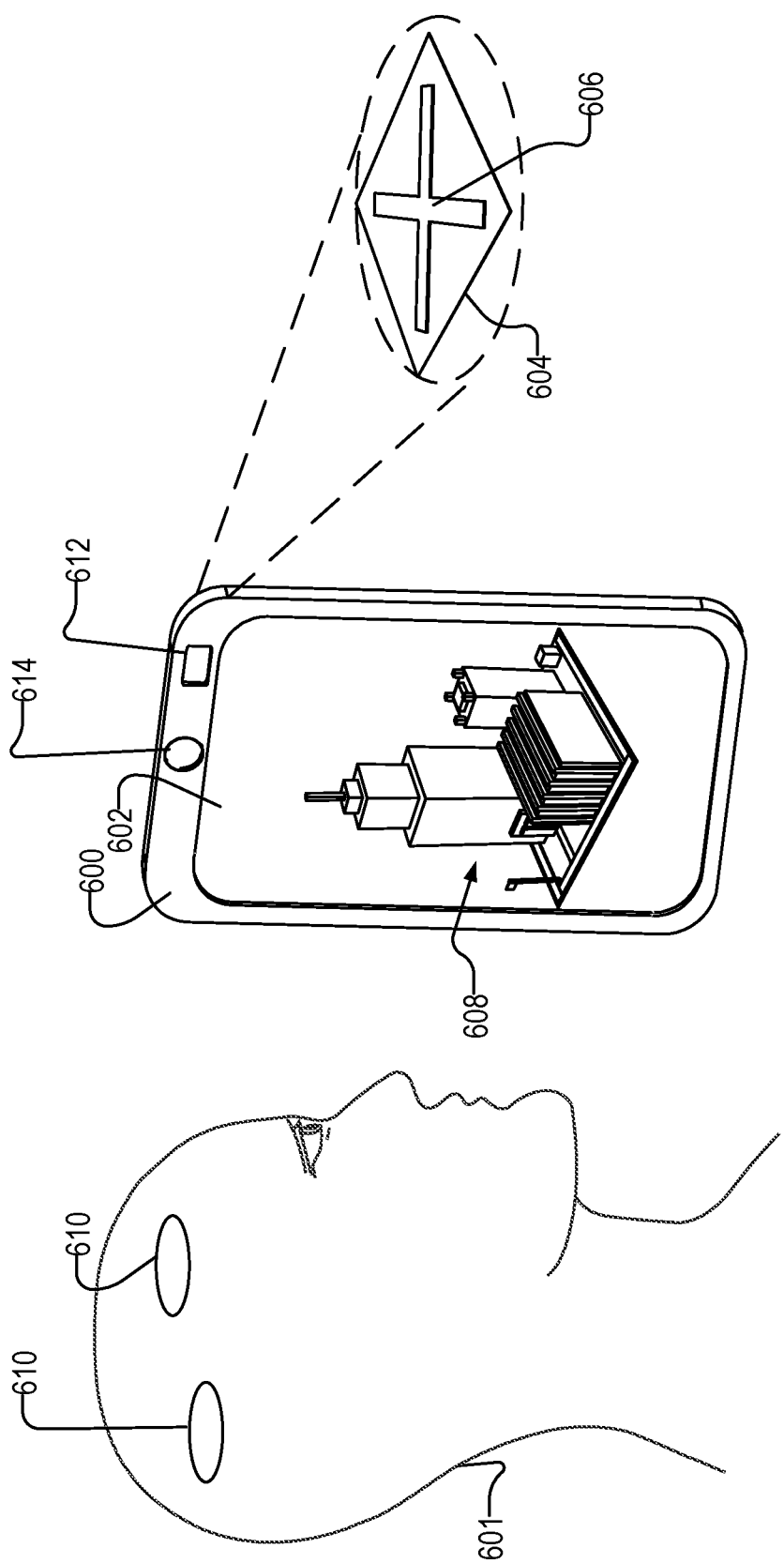
FIG. 6A is a diagram illustrating an example of a visualization of a selection of a virtual object in the device of FIG. 1 based on intent, according to some example embodiments.

FIG. 6A is a block diagram illustrating an example of a visualization of a virtual object in the device based on intent, according to some example embodiments. A user 601 is equipped with sensors 610, such as electrodes that are positioned on the scalp of the user 601. As previously described, sensors 610 may include other types of measuring devices for measuring facial muscle activity and heart rate activity among others. Sensors 610 may be physically coupled via wires to a device 600 (e.g., mobile communication device). In another example, sensors 610 may communicate with the device 600 wirelessly using wireless communication means (e.g., Bluetooth®, ZigBee®).

The user 601 points a rear camera 612 of the device 600 towards a physical object 604 having a visual reference 606. As previously described, the visual reference 606 may include a picture, a machine-readable code, or any other identifier unique to the augmented reality application 112 in the device 600. The physical object 604 may be, for example, a page of a magazine or newspaper. In another embodiment, the physical object 604 and the visual reference 606 may be combined together (e.g., a poster or a cup). In such case, the three-dimensional physical object may be used as a visual reference. For example, a three-dimensional object such as a cup having a specific pattern or design may be used as a visual reference. The device 600 captures an image or a picture of the physical object 604 and the visual reference 606 using the rear camera 612.

The device 600 generates a visualization of a three-dimensional virtual object in a display 602 of the device 600 based on outputs from sensors 610 and the visual reference 606. For example, the device 600 may determine that the user 601 is geographically located at an architectural firm. The device 600 determines from the sensors 610 that the state of mind of the user 601 corresponds to a focused state. In another embodiment, a front facing camera 614 of the device 600 may further enhance and provide additional data on the state of mind of the user 601. For example, the device 600 may obtain a live picture of the user 601 using the front facing camera 614 to determine a smile or a frown. In another example, the front facing camera 614 may be used for facial recognition to determine the identity of the user 601. The device 600 may retrieve preferences from the user 601 such as, for example, favorite colors or items. In another example, the device 600 determines, identifies, and manipulates a virtual object to be displayed in the display 602 based on a combination of the geographic location of the device 600 (e.g., office, home, restaurant, city, country), time of capture (e.g., morning, afternoon, evening, holiday, weekend) of the visual reference 606, orientation (e.g., portrait or landscape, how close) of the device 600 relative to the visual reference 606, identification of the user 601 (e.g. using facial recognition, or login information), preferences of the user 601 (e.g., favorite color, favorite type of music) social network information (e.g., number of friends, interests, proximity of friends, postings) related to the user 601, outputs from sensors 610 (e.g., EEG brain waves, EMG muscles waves, EOG eyes waves, heart rate, blood pressure), and the visual reference 606.

The device 600 may then generate a visualization of a three-dimensional virtual object engaged with a picture of the physical object 604 based on the state of mind of the user 601. In the present example, a three-dimensional model of a building 608 is rendered on top of an image of the physical object 604 in the display 602 for a focused state. In another example, if the user's state of mind is relaxed, the device 600 may generate a three-dimensional model of a vacation home rendered on top of an image of the physical object 604 in the display 602. As such, the device 600 determines a virtual object to be displayed in the display 602 in response to the captured image of the visual reference 606 and the present state of mind of the user 601.

Figure 6B:
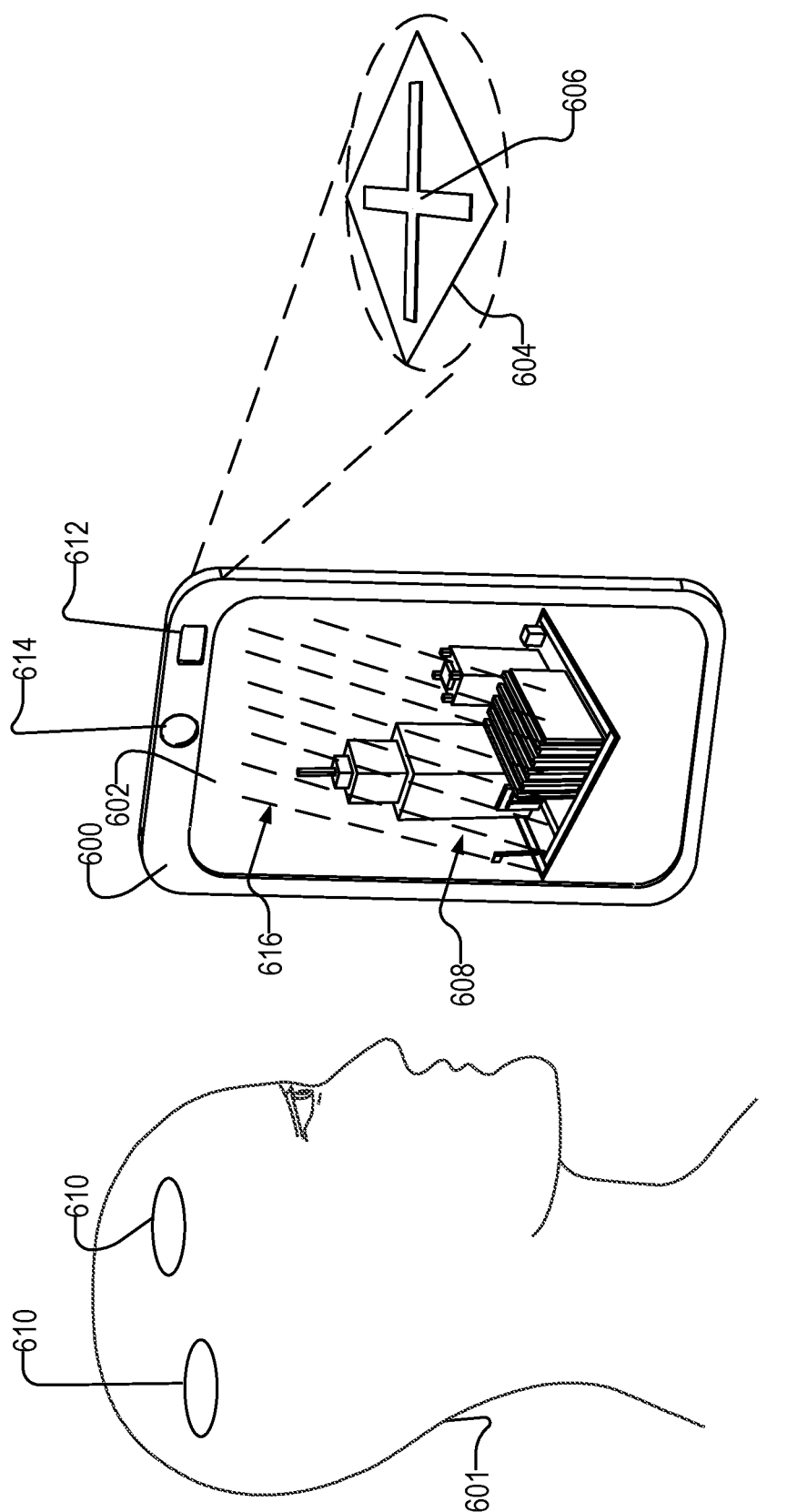
FIG. 6B is a diagram illustrating an example of a visualization of an action on an existing virtual object in the device of FIG. 1 based on intent, according to some example embodiments.

FIG. 6B is a block diagram illustrating an example of a visualization of an action on a virtual object in the device based on intent, according to some example embodiments. The device 600 determines a change in the state of mind of the user 601 (e.g., from happy to angry). The device 600 then generates a change in the visualization of the three-dimensional virtual object in the display 602 of the device 600 based on the change in the state of mind of the user 601 in response to changes in outputs from sensors 610 and the front facing camera 614. For example, rain over the building 608 may be dynamically animated in the display 602 when the device 600 detects that the user 601 has frowned and is unfocused.

As such, changes of the already displayed three-dimensional virtual object in the display 602 are determined based on the changes in the state of mind of the user 601. In another example, the color of the building 608 may change to a lighter hue when the user 601 becomes more relaxed while looking at the building 608. In another example, the texture of the building 608 may change to a rougher texture when the user 601 becomes agitated.

Figure 6C:
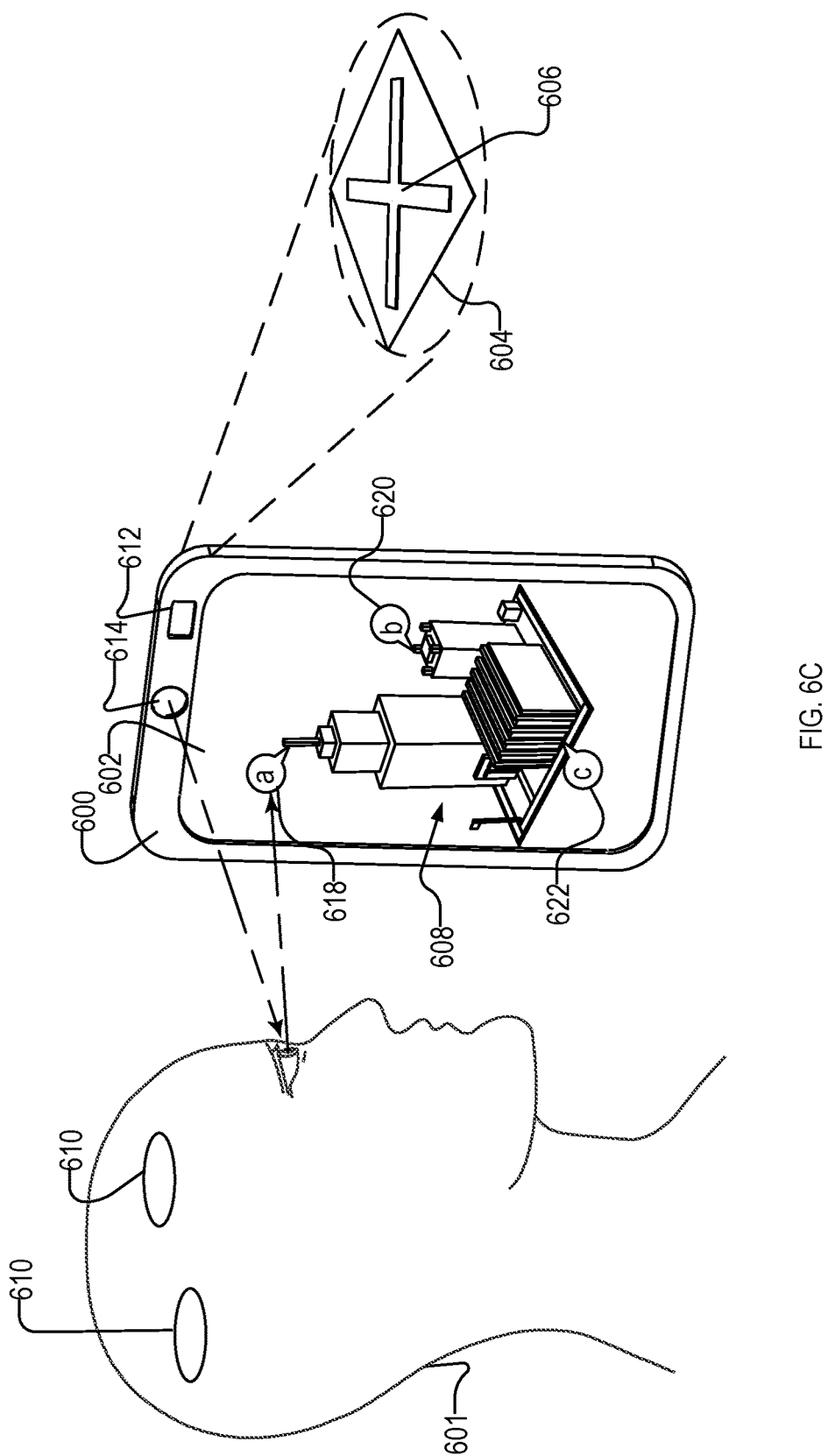
FIG. 6C is a diagram illustrating an example of a visualization of an action on an existing virtual object in the device based on intent in combination with a visual gesture, according to some example embodiments.

FIG. 6C is a block diagram illustrating an example of a visualization of an action on a virtual object in the device based on intent in combination with a visual gesture, according to some example embodiments.

The front-facing camera 614 of the device 600 may capture and monitor a gaze of the user 601. In other words, the device 600 may be capable of tracking eye movement to determine where on the display 602, the user is looking at. In another embodiment, the front-facing camera 614 of the device 600 determines the gaze of the user 601 using a combination of eye-tracking movement and head-tracking movement.

The building 608 may include points of interest icons 618, 620, 622. For example, the point of interest icon 618 may provide additional information corresponding to the location of the point of interest icon 618 relative the three-dimensional model of the building 608, when the point of interest icon 618 is triggered or otherwise selected.

In one embodiment, a state of the point of interest icon 618 may be changed to in response to the user 601 viewing the point of interest 618 and a state of mind of the user 601. For example, the point of interest icon 618 may change color based on the state of mind of the user 601.

In another embodiment, the device 600 may display more information about the point of interest icon 618 in response to determining that the user 601 is looking at the point of interest icon 618 and that the state of mind of the user 601 corresponds to a focused state. For example, a description box may pop up in the display 608 when the user 601 is looking at the point of interest icon 618 and the user 601 is determined to be in a focused state using sensors 610.

In another embodiment, the user 601 has positioned the device 600 relative to the physical object 604 such that the point of interest icon 512 is displayed in a central area of the display 602 of the device 600. In one embodiment, a state of the point of interest icon 618 may be changed to notify the user of the selection. For example, the color of the point of interest icon 618 may be changed to bring attention to a user of the device 600.

In another embodiment, the front-facing camera 614 tracks an eye movement of the user 601 viewing the building 608 in the display 602 of the device 600. The device 600 determines that the user 604 is looking at an area (e.g., flag pole) on the display 602. The area may correspond to a pre-identified location on the building 608. The pre-identified location may include a point of interest on the building 608 associated with area. For example, the device 600 detects that the user 601 is looking at the flagpole of the building 608 for a few seconds. In one example, a dialog box showing more information about the flag pole may be displayed. In another example, the device 600 may generate any other action associated with the pre-identified location on the building 608.

In another embodiment, the device 600 may include a transparent display (not shown) that may be used to identify a physical object or a particular location on the physical object. In one example, the transparent display may be mounted to a head of the user (e.g., via eyeglass mount or headgear mount). In another example, the transparent display may be a handheld device that the user 601 holds and looks through to see a physical object behind the transparent display. The rear facing camera of the device 600 may recognize physical objects being looked by the user (e.g., by comparing an image of the physical object with a reference image). In particular, the position and orientation of the transparent display with respect to the user and the physical object may be used to determine a line of sight of the user. Using the determined line of the sight of the user, the device can identify in real time the physical objects being looked and in particular which part of the physical object is being looked.

Once the device 600 identifies that the recognized physical object or the part of the recognized physical object corresponds to a preidentified physical object or pre-identified part of the physical object, the device may trigger a corresponding action (e.g., sending an email, generating a sound, etc.) based on the state of mind of the user 601. For example, the device 600 detects the user 601 looking through the transparent display to a bottom portion of a television set. The device 600 recognizes the television set and determines that the bottom portion of the television set (being looked at by the user 601) is associated with an action corresponding to generating a communication to the television set to switch the TV on or off. If the user 601 has looked at the bottom portion of the television set for at least several seconds and the state of mind indicates that the user is focused, the device 600 generates a corresponding signal to turn on or off the television set.

In another example, the device 600 may display a virtual menu of TV channels overlaid on the TV based on the state of mind of the user 601. For example, if the user is excited, the menu of TV channels may include sports channels and action movies. In another example, the user 601 may look through a transparent display of the device 600 to a radio device. Similarly, a virtual menu of music channels may be displayed over the radio device based on the state of mind of the user 601. For example, the device 600 may display a virtual menu of classical or relaxing music channels when sensors 610 indicate that the user 601 is relaxed or sleepy.

Figure 7:
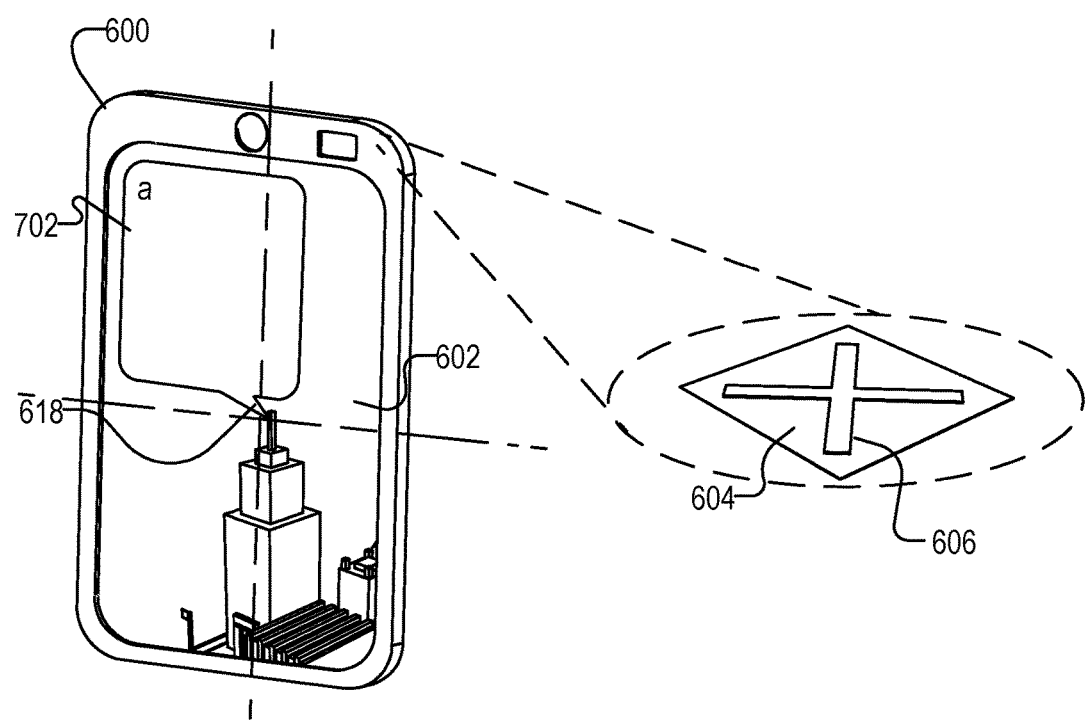
FIG. 7 is a diagram illustrating an example of a visual gesture to trigger a change in a state of a feature of a virtual object in the display of the device of FIG. 1, according to some example embodiments.

FIG. 7 is a block diagram illustrating an example of a visual gesture to trigger a change in a state of a feature of the three-dimensional virtual object in the display of the device, according to some example embodiments. For example, when the device 600 detects that the point of interest icon 618 has been present in the focus area (e.g., center area of the display 602) for at least a predetermined amount of time, an action is triggered to change a state of the point of interest icon 618 based on the state of mind of the user 601. For example, a dialog box 702 may pop up, or another action (e.g., playing a media file, saving the point of interest 618, emailing a description) corresponding to the point of interest icon 618 and the state of mind of the user 601 may be displayed on the device 600. In another example, the content of the dialog box 702 may be based on the state of mind of the user 601.

Figure 8:
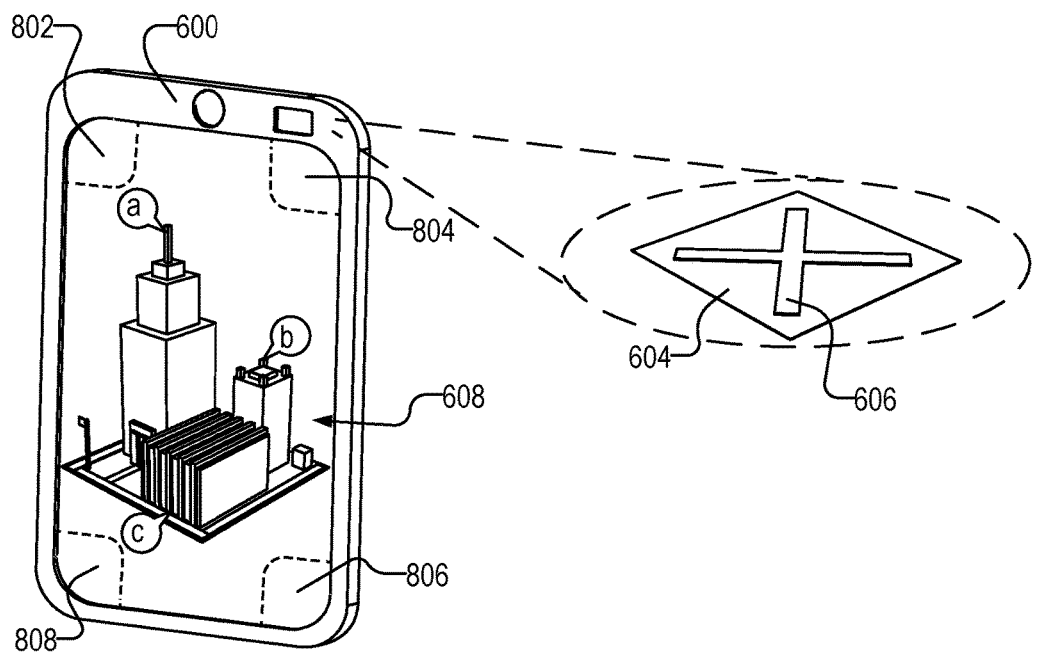
FIG. 8 is a diagram illustrating an example of a visual gesture to focus on a feature of a virtual object in the device of FIG. 1, according to some example embodiments.

FIG. 8 is a block diagram illustrating an example of a visual gesture to focus on a feature of the three-dimensional object in the device, according to some example embodiments. For example, the focus areas of the device 600 may be located in the corners 802, 804, 806, 808 of the device 600. Each corner may be associated with a corresponding action (e.g., triggering an action such as saving a point of interest) that is also based on the state of mind of the user. For example, corner 802 may be associated with sending an email. The recipient of the email may be determined based on the state of mind of the user. If the user is happy, the email includes a template compliment email to the head architect of an architecture firm that designed the building 608. If the user is unhappy, the email may include a template complaint email to a customer service department.

Figure 9:
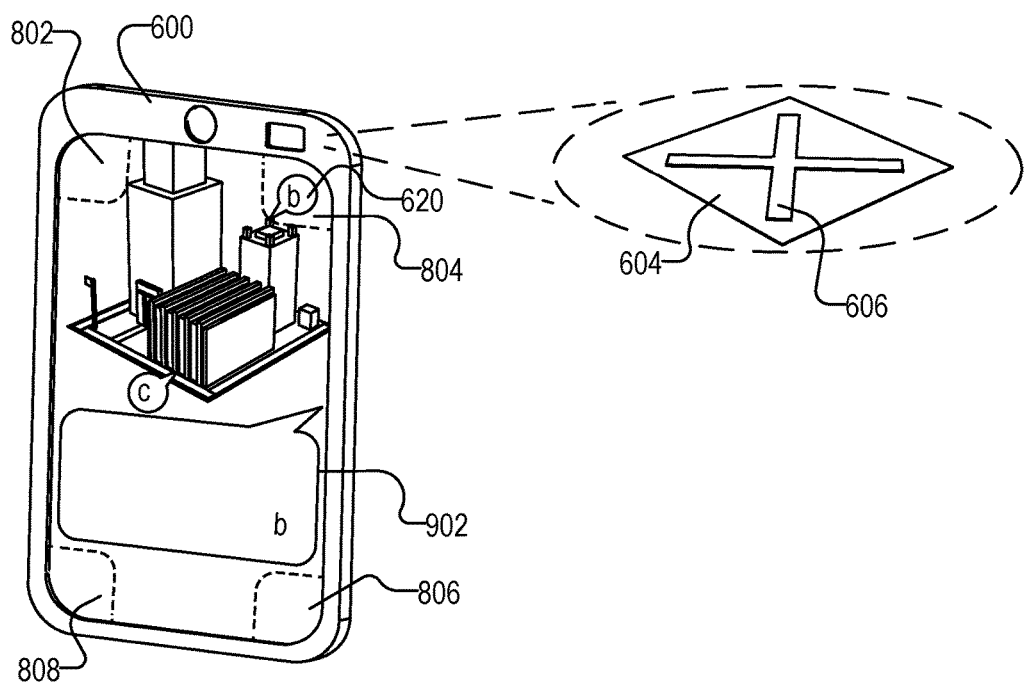
FIG. 9 is a block diagram illustrating an example of a visual gesture to trigger a change in a state of a feature of a virtual object in the device of FIG. 1, according to some example embodiments.

FIG. 9 is a block diagram illustrating an example of a visual gesture to trigger a change in a state of a feature of the three-dimensional object in the device, according to some example embodiments. For example, because the point of interest icon 620 is within the focus area of corner 802 for at least a few seconds, the augmented reality application 112 may generate a dialog box 902 to provide a description associated with the point of interest icon 510 and the present state of mind of the user. As such, the user 601 of the device 601 is able to generate actions related to the three-dimensional object in the device without having to tap on the screen or display of the device 601.

Figure 10:
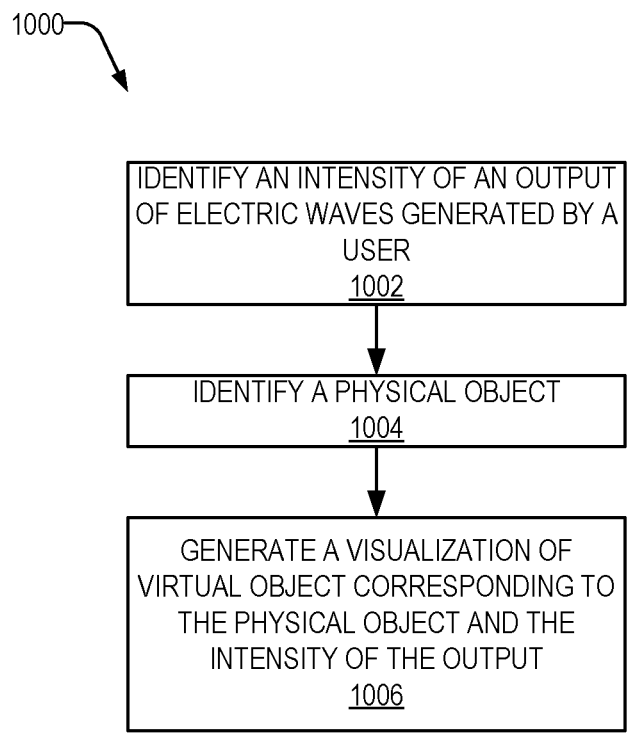
FIG. 10 is a flowchart illustrating an example operation of the visualization application of a device in performing a method for generating a virtual object based on intent, according to some example embodiments.

FIG. 10 is a flowchart illustrating an example operation of the visualization application of a device in performing a method 1000 for visualizing a virtual object based on intent, according to some example embodiments. In operation 1002, a state of mind of a user is identified based on the intensity of outputs of sensors coupled to a human. The output may include, for example, electric brain waves. In one embodiment, the operation 1002 may be performed using the electric wave application 110 of the device 100 of FIG. 1.

In operation 1004, an image of a physical object captured the device is recognized or identified. In one embodiment, the operation 1004 may be performed by the reference identifier module 302 that identifies a visual reference on the physical object.

In operation 1006, the virtual object generation module 304 generates and displays a visualization of a virtual object engaged (e.g., overlaid on top of) with an image of the physical object. The virtual object corresponds to the visual reference and the state of mind (e.g., intensity of the output of the sensors) of the user. In one embodiment, the virtual object generation module 304 renders the visualization of virtual object based a position of the display relative to the visual reference.

Figure 11:
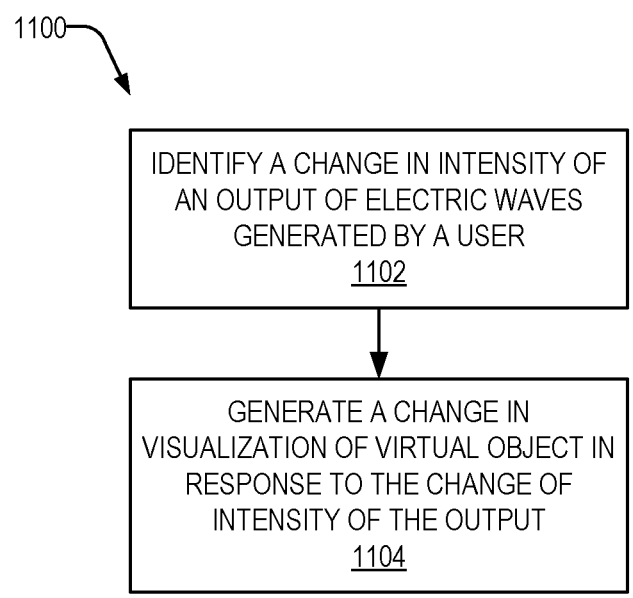
FIG. 11 is a flowchart illustrating an example operation of the visualization application of a device in performing a method for manipulating an existing virtual object based on intent, according to some example embodiments.

FIG. 11 is a flowchart illustrating an example operation of the visualization application of a device in performing a method 1100 for manipulation of a virtual object based on intent, according to some example embodiments.

In operation 1102, a change in the state of mind of a user is identified based on a change in the intensity of outputs of sensors coupled to the user. In one embodiment, the operation 1102 may be performed using the electric wave application 110 of the device 100 of FIG. 1.

In operation 1104, the virtual object generation module 304 changes a visualization of the previously displayed virtual object in the display based on the change in the state of mind of the user (e.g., change in intensity of the output of the sensors). In other words, an action may be performed on the virtual object in the display based on the change in the change in the state of mind of the user. The virtual object may be manipulated based on the change in outputs of the sensors. For example, the color of the virtual object may change from red to blue as the user becomes more relaxed. The virtual object may spin faster as the user becomes more focused. The door of a virtual car may open as the user becomes more focused on the location of the door on the display. In one embodiment, the virtual object generation module 304 renders the visualization of virtual object based a change in a position of the display relative to the visual reference.

Figure 12:
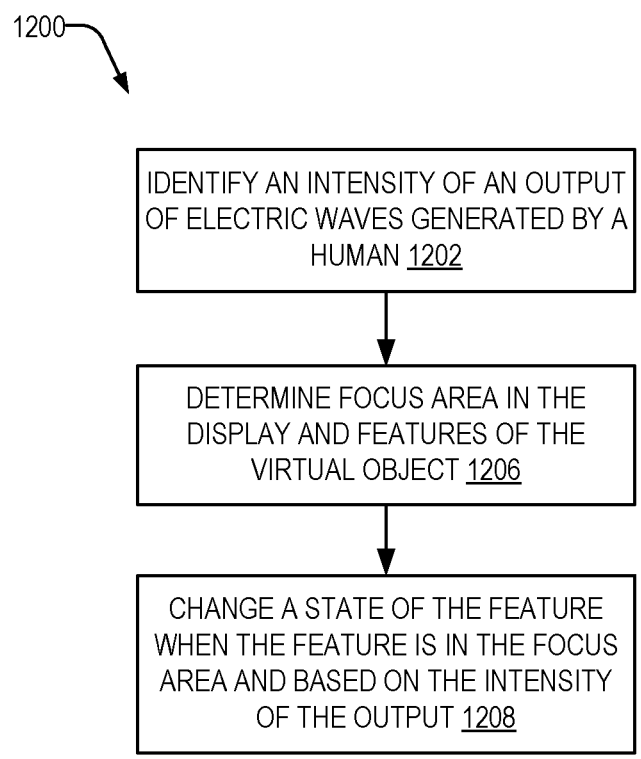
FIG. 12 is a flowchart illustrating an example operation of the visualization application of a device in performing a method for manipulating a virtual object based on intent and visual gestures, according to some example embodiments.

FIG. 12 is a flowchart illustrating an example operation of the visualization application of a device in performing a method 1200 for manipulation of a virtual object based on intent and visual gestures, according to some example embodiments.

In operation 1202, a state of mind of a user is identified based on the intensity of outputs of sensors coupled to a human. The output may include, for example, electrical brain waves. In one embodiment, the operation 1002 may be performed using the electric wave application 110 of the device 100 of FIG. 1.

In operation 1206, the visual gesture module 306 determines a focus area in the display and a feature of the virtual object. The visual gesture module 306 changes a state of the feature in response to the feature being in the focus area of the display and in response to the state of mind of the user (or a change of the state of mind).

In one embodiment, the reference identifier module 302 and the visual gesture module 306 store in a storage device of the device, a database of visual references, corresponding virtual objects, corresponding features of the virtual objects, corresponding state of mind. The features of the virtual objects change state in response being in the focus area of the display.

In one embodiment, the visual gesture module 306 changes the state of the feature in response to the feature being located within a predefined portion of the display and the state of mind of the user. The focus area corresponds to the predefined portion of the display.

In one embodiment, the predefined portion of the display comprises an area central to the display, an area adjacent to an edge of the display, an area adjacent to a corner of the display, or a user-defined area.

In one embodiment, the visual gesture module 306 changes the state of the feature in response to the feature being located within the predefined portion of the display for a time duration exceeding a time threshold and a maintained state of mind exceeding a time threshold.

In one embodiment, the visual gesture module 306 detects a presence of the feature of the three-dimensional virtual object in the focus area of the display, and changes a state of the feature when the feature is present in the focus area (and based on the state of mind of the user).

In one embodiment, the visual gesture module 306 replaces a first component of the three-dimensional virtual object in the focus area with a second component of the three-dimensional virtual object in the focus area. The feature may include an interactive object that changes state when the interactive object is in the focus area (and based on the state of mind of the user). For example, interactive object may change color when the interactive object is in the focus area.

Figure 14:
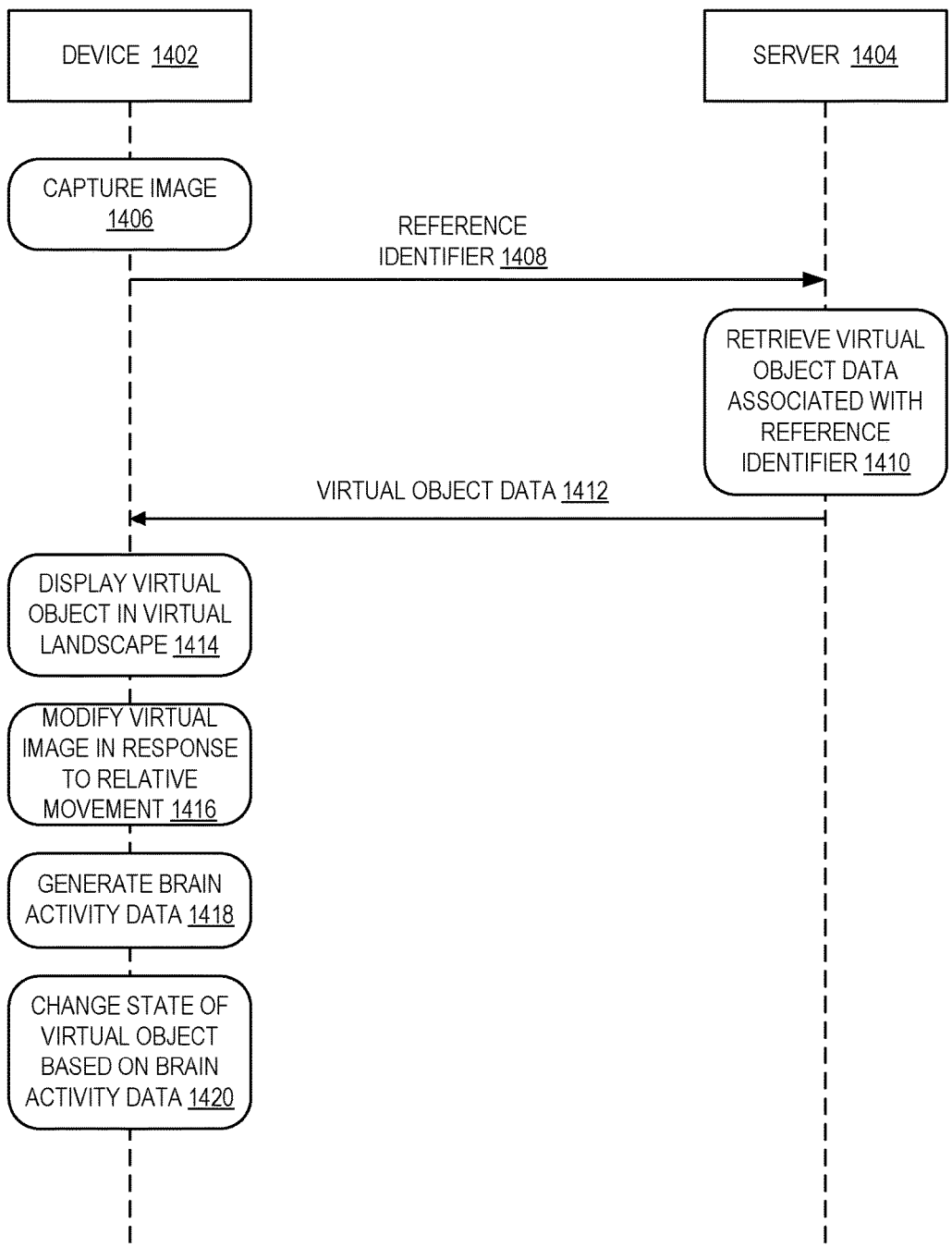
FIG. 14 is a ladder diagram illustrating an example operation for manipulating a virtual object based brain activity data, according to some example embodiments.

FIG. 14 is a ladder diagram illustrating an example operation for manipulating a virtual object based brain activity data, according to some example embodiments. A device 1402 (such as device 100) captures an image of a reference identifier from a physical object at operation 1406. At operation 1408, device 1402 communicates the reference identifier to a remove server 1404 via a network. The remote server 1404 retrieves virtual object data associated with the reference identifier. The remote server 1404 sends the virtual object data to the device at operation 1412. The device 1402 then displays the virtual image in a virtual landscape using the virtual object data at 1414. The device 1402, in response to a relative movement between the device and the physical object caused by a user, modify the virtual image at operation 1416. At operation 1418, a brain activity application of the device 1402 receives brain activity data of the user and changes a state of the virtual object in the virtual landscape based on the brain activity data at operation 1420.

Modules, Components and Logic

Certain embodiments are described herein as including logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client, or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network and via one or more appropriate interfaces (e.g., APIs).

Electronic Apparatus and System

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

A computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium

Figure 13:
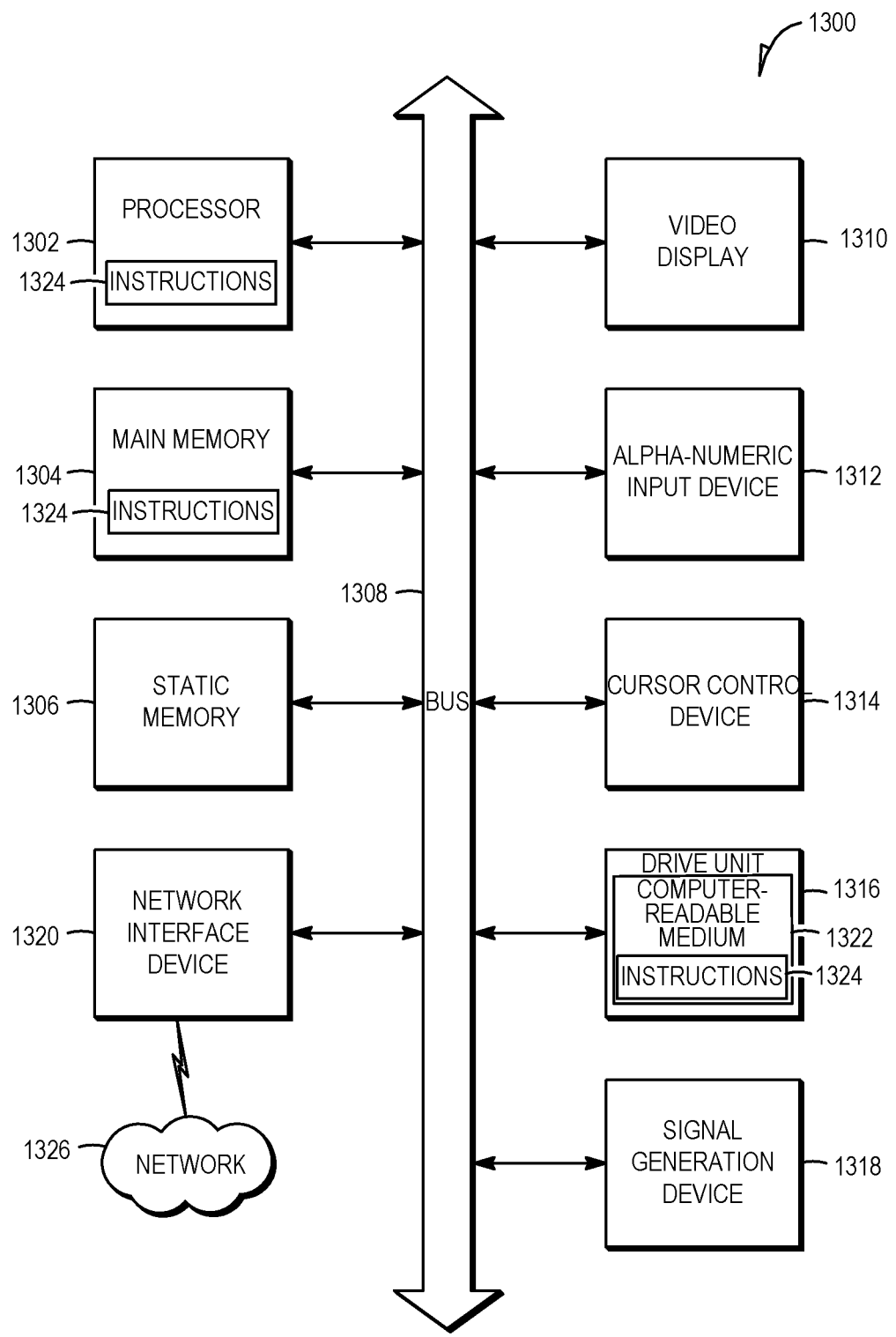
FIG. 13 is a block diagram illustrating components of a machine, according to some example embodiments, able to read instructions from a machine-readable medium and perform any one or more of the methodologies discussed herein.

FIG. 13 is a block diagram of a machine in the example form of a computer system 1300 within which instructions for causing the machine to perform any one or more of the methodologies discussed herein may be executed. In alternative embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1300 includes a processor 1302 (e.g., a central processing unit (CPU), a graphics processing unit (GPU) or both), a main memory 1304 and a static memory 1306, which communicate with each other via a bus 1308. The computer system 1300 may further include a video display unit 1310 (e.g., a liquid crystal display (LCD) or a cathode ray tube (CRT)). The computer system 1300 also includes an alphanumeric input device 1312 (e.g., a keyboard), a user interface (UI) navigation (or cursor control) device 1314 (e.g., a mouse), a disk drive unit 1316, a signal generation device 1318 (e.g., a speaker) and a network interface device 1320.

Machine-Readable Medium

The disk drive unit 1316 includes a machine-readable medium 1322 on which is stored one or more sets of data structures and instructions 1324 (e.g., software) embodying or utilized by any one or more of the methodologies or functions described herein. The instructions 1324 may also reside, completely or at least partially, within the main memory 1304 and/or within the processor 1302 during execution thereof by the computer system 1300, the main memory 1304 and the processor 1302 also constituting machine-readable media. The instructions 1324 may also reside, completely or at least partially, within the static memory 1306.

While the machine-readable medium 1322 is shown in an example embodiment to be a single medium, the term "machine-readable medium" may include a single medium or multiple media (e.g., a centralized or distributed database, and/or associated caches and servers) that store the one or more instructions 1324 or data structures. The term "machine-readable medium" shall also be taken to include any tangible medium that is capable of storing, encoding or carrying instructions for execution by the machine and that cause the machine to perform any one or more of the methodologies of the present embodiments, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices (e.g., Erasable Programmable Read-Only Memory (EPROM), Electrically Erasable Programmable Read-Only Memory (EEPROM), and flash memory devices); magnetic disks such as internal hard disks and removable disks; magneto-optical disks; and compact disc-read-only memory (CD-ROM) and digital versatile disc (or digital video disc) read-only memory (DVD-ROM) disks.

Transmission Medium

The instructions 1324 may further be transmitted or received over a communications network 1326 using a transmission medium. The instructions 1324 may be transmitted using the network interface device 1320 and any one of a number of well-known transfer protocols (e.g., HTTP). Examples of communication networks include a LAN, a WAN, the Internet, mobile telephone networks, POTS networks, and wireless data networks (e.g., WiFi and WiMax networks). The term "transmission medium" shall be taken to include any intangible medium capable of storing, encoding, or carrying instructions for execution by the machine, and includes digital or analog communications signals or other intangible media to facilitate communication of such software.

Although an embodiment has been described with reference to specific example embodiments, it will be evident that various modifications and changes may be made to these embodiments without departing from the broader spirit and scope of the present disclosure. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A device comprising:
   a first camera configured to generate an image of a physical object;
   a second camera configured to track eye movements of a user of the device;
   a display; and
   an augmented reality application implemented with a hardware processor of the device, the augmented reality application configured to:
      identify a three-dimensional virtual object based on the image of the physical object,
      render the three-dimensional virtual object in the display,
      determine a gaze of the user of the device based on the eye movements of the user of the device,
      identify a location on the three-dimensional virtual object based on the gaze of the user of the device,
      identify an interactive feature of the three-dimensional virtual object, the interactive feature corresponding to the location on the three-dimensional virtual object;
      determine that the interactive feature is located within a predefined portion of the display,
      receive brain activity data of the user in response to the gaze of the user on the identified location on the three-dimensional virtual object, and
      change a state of the interactive feature of the three-dimensional virtual object at the identified location on the three-dimensional virtual object by replacing a first component of the interactive feature of the three-dimensional virtual object in the predefined portion of the display with a second component of interactive feature of the three-dimensional virtual object in the predefined portion of the display based on the brain activity data and in response to determining that the interactive feature is located within the predefined portion of the display.

2. The device of claim 1, further comprising:
   a storage device including a database configured to store visual references, virtual objects that correspond to the visual references, and features of the virtual objects, the features of the virtual objects being configured to change components in response to the brain activity data of the user.

3. The device of claim 1, wherein the predefined portion of the display includes at least one of a central area of the display, a perimeter area adjacent to an edge of the display, a corner area adjacent to a corner of the display, and a user-defined portion of the display.

4. The device of claim 1, wherein the first component of the interactive feature of the three-dimensional virtual object is replaced with the second component of the interactive feature of the three-dimensional virtual object in response to the interactive feature being located within the predefined portion of the display for a time duration exceeding a time threshold.

5. The device of claim 1, wherein the first component of the interactive feature of the three-dimensional virtual object is replaced with the second component of the interactive feature of the three-dimensional virtual object in response to the brain activity data exceeding a threshold for a time duration exceeding a time threshold.

6. A method comprising:
generating an image of a physical object with a first camera of a device;
tracking eye movements of a user of the device with a second camera of the device;
identifying a three-dimensional virtual object based on the image of the physical object;
rendering, using a hardware processor of the device, the three-dimensional virtual object in a display of the device;
determining a gaze of the user of the device based on the eye movements of the user of the device,
identifying a location on the three-dimensional virtual object based on the gaze of the user of the device;
identifying an interactive feature of the three-dimensional virtual object corresponding to the location on the three-dimensional virtual object;
determining that the interactive feature is located within a predefined portion of the display;
receiving brain activity data of the user in response to the gaze of the user on the identified location on the three-dimensional virtual object; and
changing a state of the interactive feature of the three-dimensional virtual object at the identified location on the three-dimensional virtual object by replacing a first component of the interactive feature of the three-dimensional virtual object in the predefined portion of the display with a second component of interactive feature of the three-dimensional virtual object in the predefined portion of the display based on the brain activity data and in response to determining that the interactive feature is located within the predefined portion of the display.

7. The method of claim 6, further comprising:
storing visual references, virtual objects that correspond to the visual references, and features of the virtual objects in a database, the features of the virtual objects being configured to change components in response to the brain activity data of the user.

8. The method of claim 6, wherein the predefined portion of the display includes at least one of a central area of the display, a perimeter area adjacent to an edge of the display, a corner area adjacent to a corner of the display, and a user-defined portion of the display.

9. The method of claim 6, wherein replacing the first component of the interactive feature of the three-dimensional virtual object in the predefined portion of the display with the second component of the three-dimensional virtual object is in response to the interactive feature being located within the predefined portion of the display for a time duration exceeding a time threshold.

10. The method of claim 6, replacing the first component of the interactive feature of the three-dimensional virtual object in the predefined portion of the display with the second component of the three-dimensional virtual object is in response to the brain activity data exceeding a threshold for a time duration exceeding a time threshold.

11. A non-transitory machine-readable medium comprising instructions that, when executed by one or more processors of a machine, cause the machine to perform operations comprising:
generating an image of a physical object with a first camera of a device;
tracking eye movements of a user of the device with a second camera of the device;
identifying a three-dimensional virtual object based on the image of the physical object;
rendering, using a hardware processor of the device, the three-dimensional virtual object in a display of the device;
determining a gaze of the user of the device based on the eye movements of the user of the device,
identifying a location on the three-dimensional virtual object based on the gaze of the user of the device;
identifying an interactive feature of the three-dimensional virtual object corresponding to the location on the three-dimensional virtual object;
determining that the interactive feature is located within a predefined portion of the display;
receiving brain activity data of the user in response to the gaze of the user on the identified location on the three-dimensional virtual object; and
changing a state of the interactive feature of the three-dimensional virtual object at the identified location on the three-dimensional virtual object by replacing a first component of the interactive feature of the three-dimensional virtual object in the predefined portion of the display with a second component of interactive feature of the three-dimensional virtual object in the predefined portion of the display based on the brain activity data and in response to determining that the interactive feature is located within the predefined portion of the display.

* * * * *